United States Patent [19]

Kapralis et al.

[11] Patent Number: 4,580,547

[45] Date of Patent: * Apr. 8, 1986

[54] FLEXIBLE HEAT PACK CONTAINING SUPER COOLED SALT SOLUTION

[76] Inventors: Imants P. Kapralis, 3020 S. Punta Del Este Dr., Hacienda Heights, Calif. 91745; Harry Krukle, 7023 Bevis Ave., Van Nuys, Calif. 91405

[*] Notice: The portion of the term of this patent subsequent to Dec. 17, 2002 has been disclaimed.

[21] Appl. No.: 651,160

[22] Filed: Sep. 17, 1984

Related U.S. Application Data

[63] Continuation-in-part of Ser. No. 617,490, Jun. 6, 1984.

[51] Int. Cl.$^4$ .............................. F24J 1/00; F24J 3/00
[52] U.S. Cl. .................... 126/263; 604/291; 422/245; 128/399
[58] Field of Search .............. 126/263, 204; 128/399–403; 604/289–291; 62/259.3; 422/245

[56] References Cited

U.S. PATENT DOCUMENTS

| | | |
|---|---|---|
| 811,750 | 2/1906 | Speiske . |
| 1,502,744 | 7/1924 | Perrault . |
| 1,656,366 | 1/1928 | Sterling et al. . |
| 1,894,775 | 1/1933 | Levenson . |
| 2,157,169 | 5/1939 | Foster ................................ 126/204 |
| 2,827,438 | 3/1958 | Broadly ............................... 252/70 |
| 3,093,308 | 5/1961 | Snelling ................................ 236/1 |
| 3,175,558 | 3/1965 | Caillouette et al. ............... 128/403 |
| 3,223,081 | 12/1965 | Hunt ................................... 126/360 |
| 3,463,161 | 8/1969 | Andrassy ............................ 128/403 |
| 3,475,239 | 10/1969 | Fearon et al. ....................... 169/109 |
| 3,536,058 | 10/1970 | Hearst ................................. 126/204 |
| 3,550,578 | 12/1970 | Fearon ................................ 126/263 |
| 3,640,283 | 2/1972 | Bhatia et al. ........................ 128/399 |
| 3,854,156 | 12/1974 | Williams ................................. 5/347 |
| 3,951,127 | 4/1976 | Watson et al. ....................... 126/206 |
| 4,077,390 | 3/1978 | Stanley ................................ 126/263 |
| 4,379,448 | 4/1983 | Kapralis ............................. 126/263 |
| 4,460,546 | 7/1984 | Kapralis et al. .................... 422/243 |

FOREIGN PATENT DOCUMENTS

82/00417  2/1982  European Pat. Off. ........... 128/403

*Primary Examiner*—J. L. Kruter
*Attorney, Agent, or Firm*—William W. Haefliger

[57] ABSTRACT

A heat producing apparatus includes a plastic container having flexible walls which are interconnected along a linear zone or zones; a supercooled salt solution is in the container, to be triggered and crystallized, to produce heat; and a trigger floats in the solution relative to the linear zone, and includes a bendable trigger strip, and a multiple member frame confining the strip, the frame and trigger movable together, relative to the linear zone or zones.

27 Claims, 9 Drawing Figures

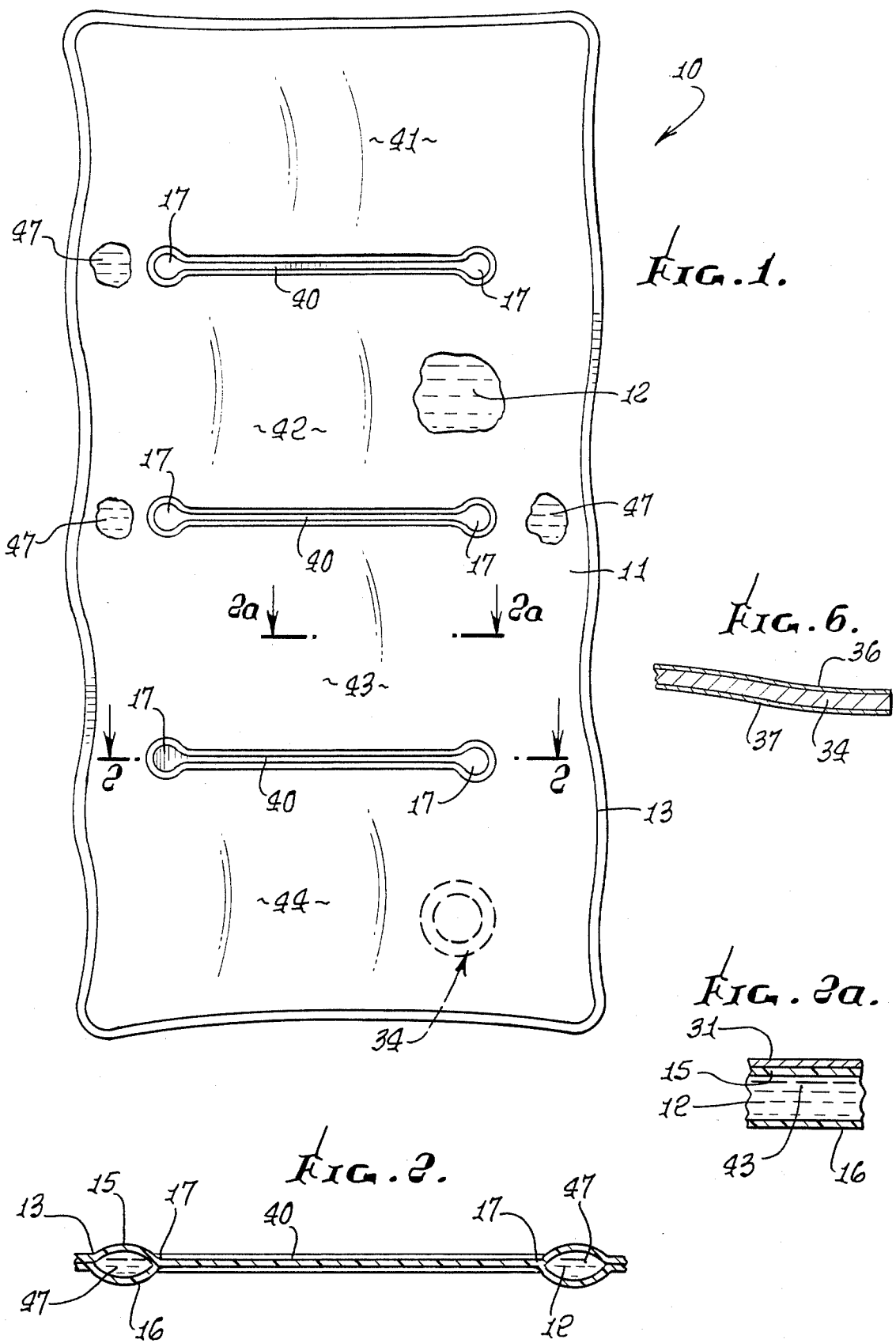

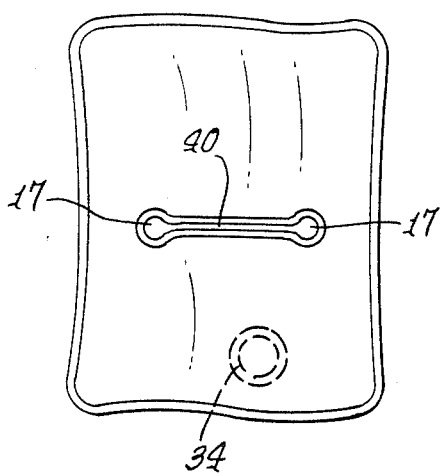
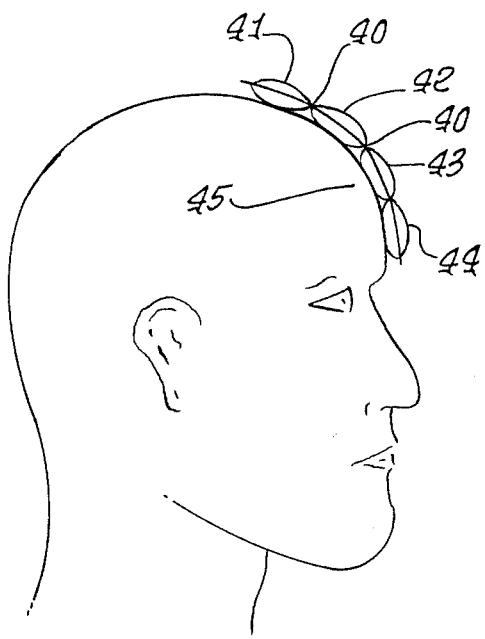
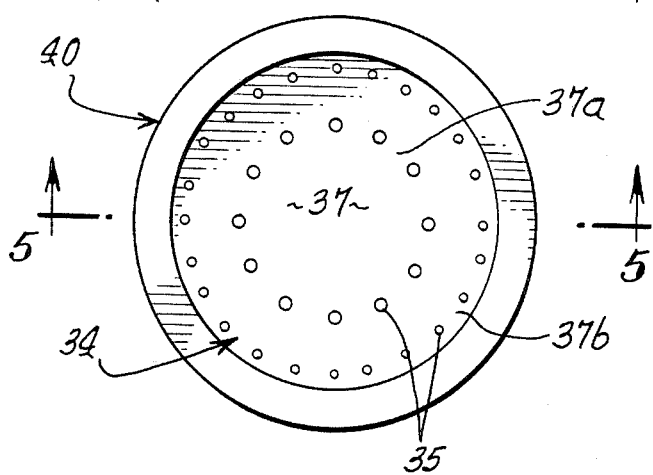
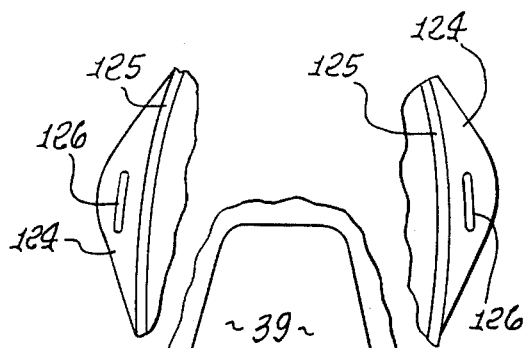
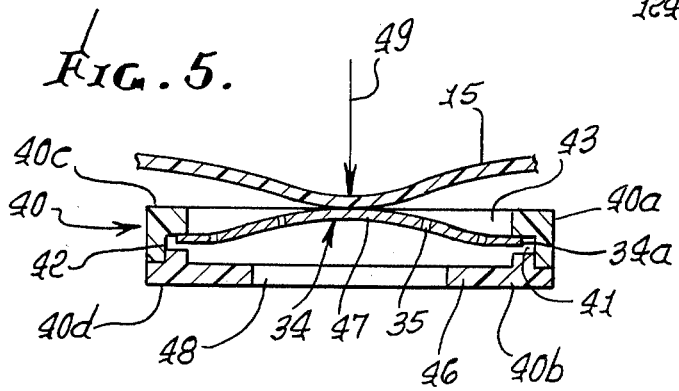

FLEXIBLE HEAT PACK CONTAINING SUPER COOLED SALT SOLUTION

BACKGROUND OF THE INVENTION

This invention relates generally to heat packs, and more particularly to flexible and foldable apparatus containing a supercooled salt solution that controllable crystallizes to produce heat. This application is a continuation-in-part of our prior application Ser. No. 617,490 filed June 6, 1984.

Heat packs incorporating unusually advantageous trigger constructions are described in our U.S. Pat. Nos. 4,379,448 and 4,460,546. There is need for a heat pack construction that is enlarged that retains the salt solution throughout the pack even though the pack is held vertically; and that is foldable and conformable to curved body contours. Also, there is need for a trigger that conforms to such a heat pack, as by floating to different portions thereof and which is activatable in such different portions and positions.

SUMMARY OF THE INVENTION

It is a major object of the invention to provide improved apparatus meeting the above needs. Basically, the improved apparatus comprises:

(a) a generally flat plastic container having opposed plastic walls forming opposite sides, the walls having edge portions which are interconnected, (b) the container containing a supercooled salt solution adapted for triggering of the solution to initiate crystallization accompanied by exothermic heat production, (c) the container being flexible so as to be manually deformable, (d) the plastic walls also interconnected along at least one linear zone spaced from said edge portions to limit displacement of the walls relatively away from one another and to form solution containing pockets between said linear zone or zones and said edge portions.

Further, and as will appear, the opposite walls may be connected together at heat sealed buttons between which at least one of said zones extends, said zone or zones also being heat sealed; the buttons may be arranged in pairs, each said zone extending between the buttons of a pair; and multiple of the linear zones may extend in generally parallel relation to enable folding of the apparatus in all states of the solution.

Further, a trigger may be located in the container and movable in a pocket generally lengthwise of at least one of said zones, force being transmissible to the trigger via a container wall portion closest to the trigger, to deform the trigger and thereby initiate said crystallization; and the trigger may comprise a thin bendable metallic strip having a perimeter, and a protective frame extending about and loosely confining said perimeter, whereby the strip is free to move about relative to the frame. The trigger may be activated in any position it randomly assumes, and the construction of the frame and floating of the trigger preventing rupture of the foldable container.

These and other objects and advantages of the invention, as well as the details of an illustrative embodiment, will be more fully understood from the following specification and drawings, in which:

DRAWING DESCRIPTION

FIG. 1 is a plan view of apparatus incorporating the invention;

FIG. 1a is a view of modified apparatus;

FIG. 2 is an enlarged view section on lines 2—2 of FIG. 1, and with added structures;

FIG. 2a is an enlarged view in section on lines 2a-2c of FIG. 1;

FIG. 3 is a side elevation showing use of apparatus of FIG. 1;

FIG. 4 is a plan view of a trigger;

FIG. 5 is an enlarged section on lines 5—5 of FIG. 1;

FIG. 6 is a fragmentary view of a trigger in section, and

FIG. 7 is a modification.

DETAILED DESCRIPTION

In FIGS. 1 and 2, heat producing apparatus 10 includes a flexible plastic container 11, which is generally flat and extends or is held to hang vertically. It contains a supercooled solution 12, one example being aqueous sodium acetate, as referred in U.S. Pat. No. 4,460,546. The container may consist of translucent or transparent plastic, such as PVC, polyethylene and polyethylene coated polypropylene. The opposite thin walls 15 and 16 of the container are typically bonded or heat sealed together at peripheral edge portions, as indicated at 13, whereby the solution 12 is contained against leakage. The container and solution 12 are manually deformable prior to triggering of the exothermic reaction, and during the reaction.

It will be noted that the plastic walls 15 and 16 are also interconnected at and along at least one linear zone (see for example elongated, parallel zones 40) spaced from the edge portion 13, so as to limit displacement of the container walls away from one another, particularly where the solution pressure is greatest, i.e. at the bottom extent of the vertical container. Solution pockets are thus formed at 41, 42, 43, and 44 spaced apart at opposite sides of the linear zones 40, the enlargement of the pockets by solution pressure being limited by the bonded zones 40; thus, solution does not drain completely from uppermost pocket 41, so that exothermic salt solution remains in all pockets, for heat treatment, as for example as indicated in FIG. 3, the apparatus being applied for example to the patient's or user's forehead 45. Also, folding of the container at zones 40 is facilitated, to conform to curved contours of the user's body.

The walls are also interconnected at heat sealed buttons 17 between which at least one of the linear zone 40 extends. As shown, the buttons are arranged in pairs, each zone 40 extending between and terminating at two buttons. The buttons 17 are spaced from the edge portion 13 of the contour so that solution passageways 47 are formed between the buttons and such edge portions, whereby the solution may flow between the pockets to be well distributed in all pockets, when the container lies horizontally flat. Also, the trigger 34 to be described may pass or float between the pockets via the passageways 47, so that successive pressurization of the trigger may occur via different container wall portions, minimizing risk of wear and ruptures of the walls. Note further, that the extended zones 40 and buttons 17 distribute loading between the walls, and minimize risk of failure of these bonds by stress.

FIG. 1a is like FIG. 1 and has the same reference numberals; but only one zone 40, and two buttons 17 are provided. Container 10 may comprise a mask used on the face.

The method of use of the mask involves the steps:

(a) during such crystallization, preventing stiffening and maintaining flexibility, of said container and of the salt crystallizing therein, and (b) applying the warm flexible container to fit a contoured body to locally heat the body by heat conduction thereto.

In this regard, mask stiffening may be prevented by flexible massaging or manipulating the mask during or immediately after salt crystallization. Triggering the latter may be carried out in many different ways, as for example by transmitting sideward pressure to the container, in the form of a sharp impact. A highly advantageous triggering device 34 may be located in the container and is described below.

FIG. 2a shows the use of a heat radiation blocking layer 31 on one side of the container, the opposite side of the container to be applied to the face. Thus, heat loss is reduced, and heat is concentrated for therapeutic transmission to the face, for longer periods. As therapeutic cream may be applied to the face prior to application of the hot mask, and a protective tissue may be interposed between the face and the mask. Also, a refrigerator chilled mask like the one described (before salt crystallization therein) may be applied over the face, after the warm mask is removed, for closing skin pores following opening of same induced by the hot mask. Layer 31 may consist of insulative plastic or fabric which is flexible.

TRIGGERING

Located in the container is a trigger 34 adapted to be deformed to initiate exothermic crystallization of the salt in the solution, and for that purpose the concentration of the salt is sufficient to produce such crystallization in response to trigger bending, as will be described. The trigger may be retained in the container at one location, or the trigger may freely float.

Generally speaking, the trigger comprises a thin strip, (for example about 0.005 inches thick) such as a non-ferrous metallic disc, having a perimeter indicated at 34a in FIG. 5. Workable non-ferrous metals have been found to include beryllium copper. Beryllium copper is a copper alloy containing a small amount of beryllium and typically some nickel or cobalt. The strip has a multiplicity of a very small opening 35 formed therein, inwardly of perimeter 34a. Each opening or puncture is characterized as having opposed edges which face one another in near touching relation. Typically, the openings initially formed in the strip may be of pin-hole size. See U.S. patent application Ser. No. 177,258 filed Oct. 11, 1980.

The disc strip 34 is characterized as having two configurations between which it is bendable with snap-displacement causing the described edges to initiate progressive exothermic crystallization of the salt in the supercooled solution in the container. The user simply applies finger pressure on the container wall 15 and snap-deforms the disc 34, which causes the edges of the openings to actuate the crystallization, due to sudden deformation (as for example sudden local compression) of the solution trapped or confined in the spaces between the approximately touching edges. The snap-displacement of the nearly touching edges is found to initiate crystallization without failure or malfunction.

These purposes are served to unusual advantage by causing the disc to have dished configuration so as to "oil can" when deformed, i.e. easily snap over-center. Further the disc has a central portion 37 free of openings, and two outer annular sections 37a and 37b. The latter contain such openings, which are typically spaced inwardly from the perimeter 34a so that the latter is continuous, aiding the snap-displacement referred to.

The performance of the disc shaped strip to initiate crystallization is aided by impact orientation of the molecular structure as described in said U.S. patent application Ser. No. 177, 258, now U.S. Pat. No. 4,460,546.

The disc or strip is typically protectively coated with a noble metal, such as gold, so as not to corrode or tarnish. See the coatings 36 and 37 on opposite surface of the disc 34, in FIG. 6. The coating for example has thickness less than 0.0001 inch, and may be electroplated on the strip or disc. Gold alloy (or silver) may also be used.

FIGS. 4 and 5 show the provision of a plastic (as for example DELRIN) frame 40 about the perimeter 34a of the disc 34, to protect the disc. The ring-shaped frame includes two interconnected annular parts 40a and 40b, which loosely confine the perimeter 34a as in an annular groove 41 in the inner wall 42 of the frame, the disc edge free to move in that groove. The disc is sufficiently, or substantially completely confined within a zone 43 bounded by the frame, so that accidental triggering as by a moving surface acting on plastic container wall 15 is prevented. Zone 43 is located between planes and defined by zone annular surfaces 40c and 40d that face axially oppositely. Note also that the plastic frame prevents gouging or tearing of the plastic container by the peripheral edge of the metallic strip or disc. The edge may have shape other than circular, and the looping frame follows the shape of the strip edge. The frame allows liquid contact with all portions of the trigger.

The frame part 40b has a wall 46 opposite concave side 47 of the dished disc or strip, i.e. the strip bulges away from the wall 46. A central opening 48 in wall 46 allows fluid passage therethrough when the disc is depressed as indicated by arrow 49, and via plastic container wall 15. The disc is snap displaced relative to the frame 40.

Other form of triggering devices, or other triggering techniques, may be employed.

In FIG. 7, the modified nose and mouth openings are combined as one as indicated at 39, in mask 10'. Also, the plastic strap 21 is eliminated, and plastic ears 124 integral with opposite edges 125 of the mask having openings 126 to receive a suitable retainer bond. The plastic container is indicated at 111, and otherwise has the same construction as in FIGS. 1 and 2.

We claim:

1. A heat producing apparatus, comprising
   (a) a generally flat plastic container having opposed plastic side walls forming opposite sides, the walls having edge portions which are interconnected,
   (b) the container containing a supercooled salt solution adpated for triggering of the solution to initiate crystallization accompanied by exothermic heat production,
   (c) the container being flexible so as to be manually deformable, to prevent stiffening and maintaining flexibility of the container during said crystallization, (d) the plastic walls also interconnected along at least one elongated linear zone spaced from said edge portions to limit displacement of the walls relatively away from one another and to form solution containing pockets between said linear zone or zones and said edge portions, (e) and including a trigger strip in the container to which force is transmissible via a side wall to deform the trigger strip, thereby to initiate said crystallization, and a frame within the container loosely and peripherally supporting the trigger strip to allow the trigger strip to deform relative to the frame, the frame being free to move with the trigger strip in the container, said frame extending peripherally about said trigger strip.

2. The apparatus of claim 1 wherein the walls are also interconnected at heat sealed buttons between which at least one of said zones extends, said zone or zones also being heat sealed.

3. The apparatus of claim 2 wherein the buttons are arranged in pairs, each said zone extending between the buttons of a pair.

4. The apparatus of claim 3 wherein multiple of said linear zones extend in generally parallel, spaced apart relation.

5. The apparatus of claim 2 wherein the buttons are spaced from the wall edge portions to form solution passageways between said pockets.

6. The apparatus of claim 1 wherein the frame and trigger strips are sized to be movable in a pocket generally lengthwise of at least one of said zones, the frame comprising multiple members that interfit to peripherally confine the trigger strip.

7. Apparatus of claim 6 wherein said frame consists of molded plastic material loosely confining said perimeter.

8. Apparatus of claim 7 wherein said frame includes a wall extending at one side of the strip in spaced relation therewith.

9. Apparatus of claim 8 wherein the strip is metallic and has dished configuration in one of said configurations characterized as stable, and characterized in that the strip bulges away from said frame wall.

10. Apparatus of claim 6 wherein the trigger is located to move about in the container and to be visible through a transparent wall of the container.

11. Apparatus of claim 6 wherein the frame comprises two annular members that interfit to loosely confine said perimeter.

12. The apparatus of claim 6 wherein the trigger comprises a thin, bendable, metallic strip having a perimeter.

13. The apparatus of claim 12 wherein the strip has a multiplicity of pin-hole size openings therethrough.

14. Apparatus of claim 12 wherein the frame has a wall extending opposite one side of the strip, the strip having a stable configuration bulging away from said wall.

15. A heat producing apparatus comprising
(a) a generally flat plastic container having opposed plastic side walls forming opposite sides, the walls having edge portions which are interconnected, (b) the container containing a supercooled salt solution adapted for trigeering of the solution to initiate crystallization accompanied by exothermic heat production, (c) the container being flexible so as to be manually deformable, to prevent stiffening and maintaining flexibility of the container during said crystallization, (d) the plastic side walls also interconnected along at least one elongated linear zone spaced from said edge portions to limit displacement of the walls relatively away from one another and to form solution containing pockets between said linear zone or zones and said edge portions, (e) and including a trigger in the container and movable in a pocket generally lengthwise of at least one of said zones, force being transmissible to the trigger via a container wall portion closest to the trigger, to deform the trigger and thereby initiate said crystallization, the trigger comprising:
  (i) a thin, metallic strip having a perimeter,
  (ii) said strip having a multiplicity of openings formed therein, each opening characterized as having opposed edges which face one another in near touching relation,
  (iii) the strip further characterized as having configurations between which it is bendable for causing said edges to initiate progressive exothermic crystallization of said salt in the solution,
  (iv) and a non-metallic frame extending peripherally about said perimeter and mounting said strip, the frame comprising two subtantially annular members that interfit to loosely confine said perimeter.

16. Apparatus of claim 15 wherein said strip perimeter is generally circular, and said frame is generally annular.

17. Apparatus of claim 15 wherein said strip has a central portion and an outer portion surrounding said central portion, said openings located in one of said portions, one frame member defining a wall having an aperture in registration with said central portion.

18. Apparatus of claim 7 wherein said strip consists of beryllium copper.

19. Apparatus of claim 15 including a noble metal coating on the strip.

20. Apparatus of claim 19 wherein said noble metal consists essentially of gold.

21. Apparatus of claim 15 wherein the strip is in the form of a disc having two of said configurations between which the disc is bendable with snap displacement.

22. Apparatus of claim 21 wherein said openings are distributed over the disc area, said openings having pin-hole size.

23. Apparatus of claim 15 including a coating on the strip, the coating consisting of a noble metal.

24. The invention of claim 23 wherein said noble metal consists essentially of gold plated on the strip.

25. Apparatus of claim 15 wherein said strip has molecular structure which is impact oriented.

26. Apparatus of claim 15 wherein the strip is in the form of a disc.

27. The invention of claim 15 wherein said strip consists of beryllium copper.